United States Patent
Castro Palomino Laria et al.

(10) Patent No.: US 10,583,127 B2
(45) Date of Patent: Mar. 10, 2020

(54) AMINE SALT OF (1R, 3S)-3-(5-CYANO-4-PHENYL-1,3-THIAZOL-2-YLCARBAMOYL)CYCLOPENTANE CARBOXYLIC ACID

(71) Applicant: PALOBIOFARMA, S.L., Mataró-Barcelona (ES)

(72) Inventors: Julio Castro Palomino Laria, Mataró-Barcelona (ES); Juan Camacho Gómez, Mataró-Barcelona (ES)

(73) Assignee: PALOBIOFARMA, S.L., Mataró-Barcelona (ES)

( * ) Notice: Subject to any disclaimer, the term of this patent is extended or adjusted under 35 U.S.C. 154(b) by 0 days.

(21) Appl. No.: 16/491,185

(22) PCT Filed: Mar. 6, 2018

(86) PCT No.: PCT/EP2018/055512
§ 371 (c)(1),
(2) Date: Sep. 5, 2019

(87) PCT Pub. No.: WO2018/162505
PCT Pub. Date: Sep. 13, 2018

(65) Prior Publication Data
US 2020/0030300 A1 Jan. 30, 2020

(30) Foreign Application Priority Data
Mar. 6, 2017 (EP) ..................................... 17382114

(51) Int. Cl.
*A61K 31/426* (2006.01)
*C07D 277/56* (2006.01)

(52) U.S. Cl.
CPC .......... *A61K 31/426* (2013.01); *C07D 277/56* (2013.01)

(58) Field of Classification Search
CPC ........................... C07D 277/56; A61K 31/426
See application file for complete search history.

(56) References Cited

U.S. PATENT DOCUMENTS

2010/0311703 A1   12/2010   Gonzalez et al.

FOREIGN PATENT DOCUMENTS

WO   2009044250 A1   4/2009

OTHER PUBLICATIONS

International Search Report, dated Jun. 5, 2018.
Berge, Stephen, M., et al.; "Pharmaceutical Salts," Journal of Pharmaceutical Sciences, 1977, pp. 1-19, vol. 66.
Hocher, Berthold; "Adenosine A1 receptor antagonists in clinical research and development," Kidney International, 2010, pp. 438-445, vol. 78; doi:10.1038/ki.2010204.
Haskó, György, et al.; "Adenosine receptors: therapeutic aspects for inflammatory and immune diseases," Nature Reviews; Drug Discovery; Sep. 2008, pp. 759-770, vol. 7.
Gwak, Hye-Sun, et al.; "Enhanced bioavailability of piroxicam via salt formation with ethanolamines," International Journal of Pharmaceutics, 2005, pp. 156-161, vol. 297.
Farag Badawy, Sherif I.; "Effect of salt form on chemical stability of an ester prodrug of a glycoprotein IIb/IIIa receptor antagonist in solid dosage forms," International Journal of Pharmaceutics, 2001, pp. 81-87, vol. 223.

*Primary Examiner* — Karen Cheng
(74) *Attorney, Agent, or Firm* — Tristan A. Fuierer; Olive Law Group, PLLC

(57) ABSTRACT

The present invention relates to the tromethamine salt of (1R,3S)-3-(5-cyano-4-phenyl-1,3-thiazol-2-ylcarbamoyl) cyclopentane carboxylic acid, a process for obtaining said salt, combination products and pharmaceutical compositions comprising said salts and their medical uses, in particular for the treatment or prevention of diseases known to ameliorate by $A_1$ adenosine receptor antagonism.

17 Claims, 4 Drawing Sheets

AMINE SALT OF (1R,3S)-3-(5-CYANO-4-PHENYL-1,3-THIAZOL-2-YLCARBAMOYL)CYCLOPENTANE CARBOXYLIC ACID

CROSS-REFERENCE TO RELATED APPLICATIONS

This application is filed under the provisions of 35 U.S.C. § 371 and claims the priority of International Patent Application No. PCT/EP2018/055512 filed on 6 Mar. 2018 entitled "AMINE SALT OF (1R,3S)-3-(5-CYANO-4-PHENYL-1,3-THIAZOL-2-YLCARBAMOYL) CYCLOPENTANE CARBOXYLIC ACID" in the name of Julio CASTRO PALOMINO LARIA, et al., which claims priority to European Patent Application No. 17382114.1, filed on 6 Mar. 2017, both of which are hereby incorporated by reference herein in their entirety.

DESCRIPTION

Field of Invention

The present invention is related to a new amine salt of (1R,3S)-3-(5-cyano-4-phenyl-1,3-thiazol-2-ylcabamoyl)cyclopentane carboxylic acid, which is an adenosine $A_1$ adenosine receptor antagonist. Particularly, the present invention is directed to (1R,3S)-3-(5-cyano-4-phenyl-1,3-thiazol-2-ylcabamoyl)cyclopentane carboxylic acid tromethamine salt. Said salt is useful for the treatment or prevention of diseases known to be ameliorated by antagonism of the $A_1$ adenosine receptor.

Background of Invention

Adenosine $A_1$ receptor antagonists are useful for the treatment or prevention of various diseases including hypertension, heart failure, ischemia, supraventricular arrhythmia, acute renal failure, myocardial reperfusion injury, asthma, allergic reactions including rhinitis and urticaria, scleroderma and autoimmune diseases, such as multiple sclerosis. (Hocher, B, *Adenosine A1 receptor antagonists in clinical research and development*, Kidney International (2010) 78, 438-445 and references therein; Hasko, G et al, *Adenosine receptors: therapeutic aspects for inflammatory and immune diseases*, Nature Reviews, volume 7, September 2008, 759 and references therein).

Specifically, patent application WO 2009/044250 A1 discloses 5-cyano-1,3-thiazole derivatives, which are potent $A_1$ adenosine receptor antagonists and which are useful in the treatment of the above-mentioned diseases. In said patent application, 3-(5-cyano-4-phenyl-1,3-thiazol-2-ylcarbamoyl)cyclopentane carboxylic acid is disclosed, in particular the (1R,3S) stereoisomer, whose structure is shown below:

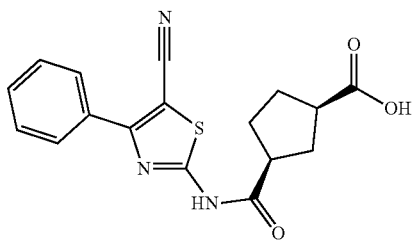 [SMILES: N#Cc1sc(NC(=O)[C@H]2CC[C@@H](C(=O)O)C2)nc1-c1ccccc1]

Pharmaceutically acceptable salts of 5-cyano-1,3-thiazole derivatives are generically mentioned in the cited document. Pharmaceutically acceptable bases for forming salts with 5-cyano-1,3-thiazole derivatives described therein are alkali metal hydroxides (for example sodium or potassium) and organic bases, such as alkylamines, arylalkylamines and heterocyclic amines. However, said document does not specify any particular salt.

Although (1R,3S)-3-(5-cyano-4-phenyl-1,3-thiazol-2-ylcarbamoyl)cyclopentane carboxylic acid has shown suitable pharmacological activity, said compound exhibits certain levels of hygroscopicity which may compromise its stability and therefore its pharmaceutical development.

Several properties can be altered by salt formation, such as solubility, dissolution rate, bioavailability (Gwak H S et al, *Enhanced bioavailability of piroxicam via salt formation with ethanolamines*, Int J Pharm 2005; 297:156-161), hygroscopicity, flavor and physical and chemical stability, among others (Farag Badawy S I, *Effect of salt form on chemical stability of an ester prodrug of a glycoprotein IIb/IIIa receptor antagonist in solid dosage forms*, Int J Pharm 2001; 223:81-87).

Given the availability of a large number of pharmaceutically acceptable counterions and the lack of correlation between the nature of a pharmaceutically acceptable counterion with the final properties of the corresponding salt, salt selection process is difficult and its results are, a priori, unpredictable.

There is a need to provide a salt which improves the physicochemical and pharmaceutical properties of (1R,3S)-3-(5-cyano-4-phenyl-1,3-thiazol-2-ylcarbamoyl) cyclopentane carboxylic acid, in particular a salt which improves the hygroscopicity, without affecting negatively other important parameters, such as crystalinity or bioavailability of active compound. In particular, it is necessary to reduce the hygroscopicity of (1R,3S)-3-(5-cyano-4-phenyl-1,3-thiazol-2-ylcarbamoyl) cyclopentane carboxylic acid under usual conditions of drug storage (<75% RH), and at the same time ensuring good levels of stability and solubility thereof, to obtain an improvement in the production, handling, storage and pharmaceutical properties of said acid.

SUMMARY OF INVENTION

The present invention provides a tromethamine salt of (1R,3S)-3-(5-cyano-4-phenyl-1,3-thiazol-2-ylcarbamoyl) cyclopentane carboxylic acid with improved physicochemical, pharmacokinetics and pharmaceutical properties in comparison to the corresponding free acid and to other salts.

After profiling a considerable number of alternative salts of (1R,3S)-3-(5-cyano-4-phenyl-1,3-thiazol-2-ylcarbamoyl) cyclopentane carboxylic acid, the inventors have surprisingly found that the tromethamine salt of said compound exhibits better properties of hygroscopicity, solubility and bioavailability, not only with respect to compound in free acid form, but also with respect to other salts of said compound.

Additionally, the tromethamine salt is obtained in crystalline form. The improvement in the aforementioned properties implies an advantage for the processes of production, handling, and storage of said compound as well as in pharmaceutical characteristics of said product. Specifically, a significant improvement in oral bioavailability has been shown by the tromethamine salt object of the present invention, which will enable the administration of significant lower doses of the compound to achieve the target therapeutic levels.

In connection with the subject matter of the present invention, no disclosure is known in state of the art relating to the preparation and use of a particular salt of (1R,3S)-3-(5-cyano-4-phenyl-1,3-thiazol-2-ylcarbamoyl)cyclopentane carboxylic acid, and especifically the tromethamine salt of said compound or any other compound belonging to the family of compounds disclosed in patent application WO2009044250A1.

Thus, in a first aspect, the present invention relates to the tromethamine salt of (1R,3S)-3-(5-cyano-4-phenyl-1,3-thiazol-2-ylcarbamoyl)cyclopentane carboxylic acid.

In a second aspect, the present invention relates to a process for the preparation of the salt defined in the first aspect, comprising:

a) mixing (1R,3S)-3-(5-cyano-4-phenyl-1,3-thiazol-2-ylcarbamoyl)cyclopentane carboxylic acid and tromethamine in presence of a solvent, and b) isolating the resulting tromethamine salt of (1R,3S)-3-(5-cyano-4-phenyl-1,3-thiazol-2-ylcarbamoyl) cyclopentane carboxylic acid.

In a third aspect, the present invention relates to a combination product comprising the salt according to the first aspect and one or more therapeutic agents selected from the group consisting of angiotensin converting enzyme inhibitors (ACE-inhibitors), angiotensin receptor antagonists, statins, beta-blockers, calcium antagonists and diuretics.

In a fourth aspect, the present invention relates to a pharmaceutical composition comprising the salt according to the first aspect or the combination product according to third aspect and a pharmaceutically acceptable excipient.

In a fifth aspect, the present invention relates to the salt according to first aspect, the combination product according to the third aspect or the pharmaceutical composition according to the fourth aspect, for use as a medicament.

In a sixth aspect, the present invention relates to the salt according to the first aspect, the combination product according to the third aspect or the pharmaceutical composition according to the fourth aspect, for use in the treatment and/or prevention of a disease known to ameliorate by $A_1$ adenosine receptor antagonism.

In a further aspect, the present invention relates to the use of the salt according to the first aspect, the combination product according to the third aspect or the pharmaceutical composition according to the fourth aspect, in the manufacture of a medicament for the treatment and/or prevention of a disease known to ameliorate by $A_1$ adenosine receptor antagonism.

In a further aspect, the present invention relates to a method of treating and/or preventing a disease known to ameliorate by adenosine $A_1$ receptor antagonism, comprising administering to a subject in need of such treatment the salt according to the first aspect, the combination product according to the third aspect or the pharmaceutical composition according to the fourth aspect.

DETAILED DESCRIPTION OF INVENTION

Figure 1:
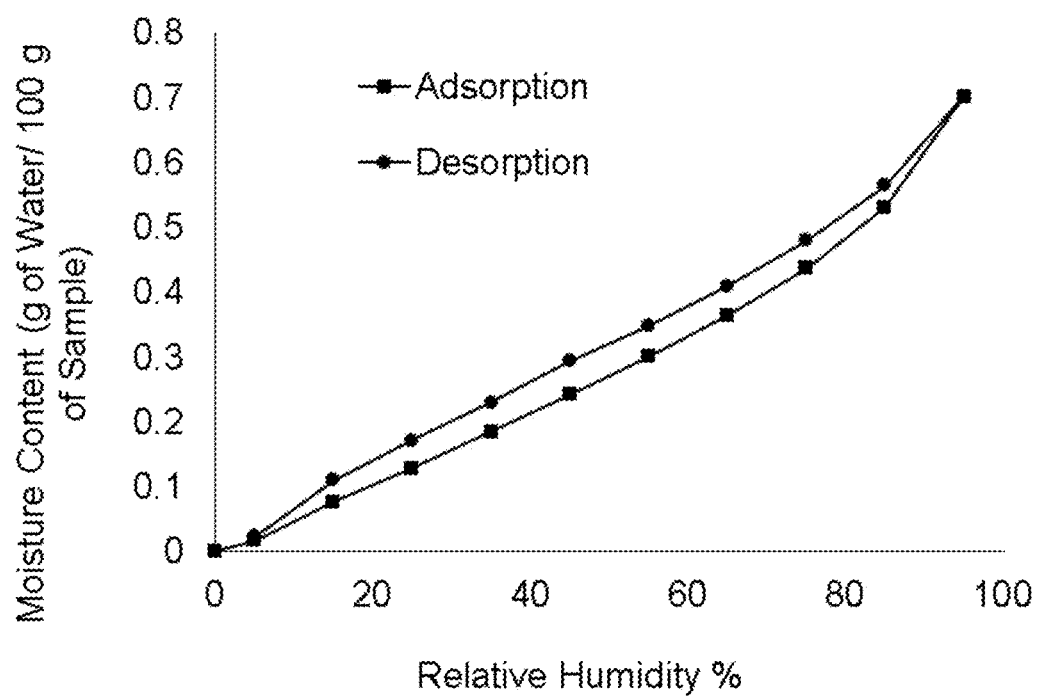
FIG. 1 illustrates DVS pattern of (1R,3S)-3-(5-cyano-4-phenyl-1,3-thiazol-2-ylcarbamoyl)cyclopentane carboxylic acid, showing the change in weight (in %) of said free acid as a function of relative humidity (RH).

The present patent application discloses several salts of (1R,3S)-3-(5-cyano-4-phenyl-1,3-thiazol-2-ylcarbamoyl) cyclopentane carboxylic acid. The following salts have been obtained from (1R,3S)-3-(5-cyano-4-phenyl-1,3-thiazol-2-ylcarbamoyl)cyclopentane carboxylic acid: tromethamine, triethanolamine, diethylamine, sodium, magnesium, lysine and arginine salts. However, from all of them, only the tromethamine salt has improved physicochemical, pharmacokinetics, and pharmaceutical properties with respect to the free acid.

Tromethamine Salt

Inventors have surprisingly found that (1R,3S)-3-(5-cyano-4-phenyl-1,3-thiazol-2-ylcarbamoyl)cyclopentane carboxylic acid tromethamine salt (IUPAC name: (1,3-dihydroxy-2-(hydroxymethyl)propan-2-aminium (1R,3S)-3-((5-cyano-4-phenylthiazol-2-yl)carbamoyl)cyclopentane-1-carboxylate) is the only salt found to have all the following advantages:

1) Stability under forced conditions: no cristallinity changes, colour or any other change in the aspect were observed in obtained solid, unlike, for example, the triethanolamine salt, which changed color and became compacted.
2) Hygroscopicity: it shows less hygroscopicity than the free acid and other similar salts as for example, the triethanolamine salt, particularly in the usual storage conditions of drugs (<75% RH).
3) Solubility: it has substantially better solubility than the free acid and than all the other salts studied, particularly better solubility than the similar salts of triethanolamine and diethylamine.
4) Bioavailability: Specially surprising has been the improvement of the tromethamine salt in the the oral exposure and bioavailability compared to the free acid and also to other structurally similar salts, like triethanolamine salt.

Therefore, said tromethamine salt offers advantages for the preparation of solid dosage forms, containing the pharmacologically active compound, facilitating its manipulation and allowing a better dosage regimen. In addition, the tromethamine salt object of the present invention possesses greater solubility in water than the free acid, thus providing a more feasible compound to be used in the preparation of aqueous pharmaceutical forms containing the pharmacologically active compound, suitable for parenteral administration.

(1R,3S)-3-(5-cyano-4-phenyl-1,3-thiazol-2-ylcarbamoyl) cyclopentane carboxylic acid tromethamine salt object of the present invention is a stable solid, even under forced stability conditions. This salt is less hygroscopic than free acid, specially up to 75% RH, as it can be seen in the examples when comparing the variation in the moisture content reached by the tromethamine salt (0.17% at 75% RH) with that of the free acid (0.43% at 75% RH).

The triethanolamine salt was a solid that slightly changed color and became compacted during stability test, showing thus some degree of hygroscopicity. Hygroscopicity analyses confirmed that this salt is hygroscopic reaching a 3.44% of variation in the moisture content at 75% RH.

The diethylamine salt showed some degradation during the stability test. Therefore, said salt is considered lacking stability and additional studies were not performed with it.

Additionally, others salts were prepared, for example, (1R,3S)-3-(5-cyano-4-phenyl-1,3-thiazol-2-ylcarbamoyl) cyclopentane carboxylic acid sodium salt, which did not have good stability, changed color and showed evident hygroscopicity; therefore, sodium salt was inadequate to achieve an improvement in the various physical, chemical and pharmaceutical parameters studied with respect to the free acid.

The magnesium salt was very hygroscopic (the amount of water adsorbed was proportional to the relative humidity (RH)), reaching 18% of variation in the moisture content at 75% RH.

As evidenced, the only salt showing an improvement in stability, hygroscopicity, bioavailability and solubility with respect to the free acid is the trometamine salt.

Therefore, the first aspect of the present invention is directed to the tromethamine salt of (1R,3S)-3-(5-cyano-4-phenyl-1,3-thiazol-2-ylcarbamoyl)cyclopentane carboxylic acid which has the following general formula:

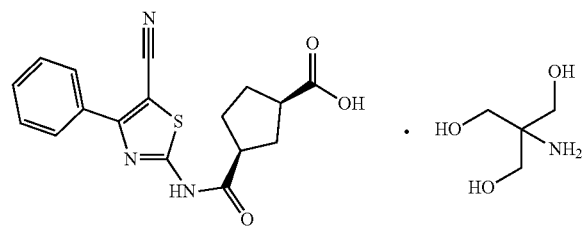

The term "salt" refers to an assembly of (1R,3S)-3-(5-cyano-4-phenyl-1,3-thiazol-2-ylcarbamoyl) cyclopentane carboxylic acid being in an ionic form (as an anion) and a counterion (a cation).

In a preferred embodiment, tromethamine and (1R,3S)-3-(5-cyano-4-phenyl-1,3-thiazol-2-ylcarbamoyl)cyclopentane carboxylic acid are in 1:1 molar ratio, that is for each mole of tromethamine present in the salt, there is one mole of (1R,3S)-3-(5-cyano-4-phenyl-1,3-thiazol-2-ylcarbamoyl) cyclopentane carboxylic acid.

In another preferred embodiment, the tromethamine salt of the present invention exhibits a crystalline form characterized by X-ray powder diffraction (XRPD) pattern comprising at least 5 2θ° peaks selected from the XRPD peak set of 8.7, 12.3, 18.0, 18.4, 21.7 and 26.1±0.20 2θ°, preferably comprising 2θ° peaks at 8.7, 18.0, 18.4, 21.7 and 26.1, ±0.20 2θ°.

In a more preferred embodiment, the tromethamine salt of the present invention exhibits a crystalline form characterized by X-ray powder diffraction (XRPD) pattern comprising 2θ° peaks at 8.7, 12.3, 13.0, 13.4, 16.3, 16.8, 17.3, 18.0, 18.4, 19.5, 20.9, 21.7, 23.8, 24.6 and 26.1±0.20 2θ°.

General Process of Preparation of Tromethamine Salt

In another aspect, the present invention is referred a process for the preparation of tromethamine salt object of the present invention, comprising:
  a) mixing (1R,3S)-3-(5-cyano-4-phenyl-1,3-thiazol-2-ylcarbamoyl)cyclopentane carboxylic acid and tromethamine in presence of a solvent, and
  b) isolating (1R,3S)-3-(5-cyano-4-phenyl-1,3-thiazol-2-ylcarbamoyl)cyclopentane carboxylic acid, tromethamine salt.

Step a) comprises mixing (1R,3S)-3-(5-cyano-4-phenyl-1,3-thiazol-2-ylcarbamoyl) cyclopentane carboxylic acid and tromethamine in presence of a solvent.

(1R,3S)-3-(5-cyano-4-phenyl-1,3-thiazol-2-ylcarbamoyl) cyclopentane carboxylic acid is prepared using the processes disclosed in patent application WO2009044250A1, incorporated by reference to the present document.

In a particular embodiment, in step a) the (1R,3S)-3-(5-cyano-4-phenyl-1,3-thiazol-2-ylcarbamoyl)cyclopentane carboxylic acid and tromethamine are in molar ratio of 1:1 to 1:1.5, preferably 1:1 to 1:1.2. The mixture of both compounds can be carried out, for example, by mechanical stirring. The mixture may be a solution or a suspension. Preferably step a) comprises heating the mixture of acid and tromethamine to the reflux temperature of the solvent, preferably until a solution is obtained. In a particular embodiment, the mixture is maintained, preferably at reflux temperature and with stirring, between 30 minutes and 24 hours, more preferably between 30 minutes and 5 hours, still more preferably between 1.5 hours and 2.5 hours, more preferred about 2 hours.

The solvent may be any suitable solvent to form the salt, ie, a solvent which does not react with (1R,3S)-3-(5-cyano-4-phenyl-1,3-thiazol-2-ylcarbamoyl)cyclopentane carboxylic acid or with tromethamine. Preferably, the solvent is selected from the group consisting of alkanols, aliphatic hydrocarbons, aromatic hydrocarbons, ethers, ketones, esters, dichloromethane, chloroform, dimethylsulfoxide, acetonitrile, water and mixtures thereof.

As used herein, the term alkyl includes linear or branched hydrocarbon chains, having from 1 to 12 carbon atoms, preferably from 1 to 6 carbon atoms, and no having insaturations. When the term alkyl is accompanied by an expression indicating the number of carbon atoms, such as $C_1$-$C_3$, it means that said alkyl has the indicated number of carbon atoms, such as from 1 to 3 carbon atoms.

As used herein, the term alkanol includes linear or branched alkyl chains as have been previously defined, linked to a hidroxyl group (OH). Preferred alkanols are isopropanol, propanol, ethanol, methanol, butanol, tert-butanol, isobutanol and mixtures thereof, more preferably isopropanol, propanol, ethanol, methanol and mixtures thereof.

As used herein, the term aliphatic hydrocarbons refer to compounds consisting of carbon and hydrogen atoms, saturated or with one or more insaturations (double or triple bond), for example, one, two or three insaturations, linear, branched or cyclic; preferably having 5 to 12 carbon atoms, more preferably 5 to 8 carbon atoms, and still more preferably 6 or 7 carbon atoms. Examples of aliphatic hydrocarbons are penthane, hexane, heptane, cyclopentane, cyclohexane, and mixtures thereof, among others; preferably heptane and cyclohexane and mixtures thereof.

As used herein, the term aromatic hydrocarbons refer to cyclic compounds consisting of carbon and hydrogen atoms, unsaturated, and complying with Hückel rule, preferably having 6 carbon atoms in the cycle, optionally substituted by one, two or three $C_1$-$C_3$ alkyl groups which may be the same or different. Examples of aromatic hydrocarbons are toluene and xylene and mixtures thereof.

As used herein, the term ether refers to compounds of formula R—O—R', wherein R and R' are selected from: (a) alkyl chains as have been previously defined, (b) wherein R and R' form together an alkylenic chain —$(CH_2)_m$—, being m an integer selected from 4 to 6, optionally substituted by a $C_1$-$C_3$ alkyl group, or (c) wherein R and R' form together a —$(CH_2)_n$—O—$(CH_2)_p$— group, being n and p integers independently selected from 1 to 3. Ether examples are diethyl ether, tert-butylmethyl ether, dioxane, tetrahydrofurane, methyltetrahydrofurane, and mixtures thereof, among others.

As used herein, the term ketone refers to compounds of formula R—C(=O)—R', wherein R and R' are independently selected from an alkyl radical, as has been previously defined. Examples of ketones are acetone and methylisobutylketone and mixtures thereof, among others.

As used herein, the term ester refers to a R—COOR' group, wherein R and R' are independently an alkyl radical, as been previously defined. Examples of esters are ethyl acetate and isobutyl acetate and mixtures thereof.

As used herein, the term tromethamine is used in the present document to designate the compound of formula $(HOCH_2)_3C$—$NH_2$, whose IUPAC name is 2-amino-2-(hydroxymethyl)propane-1,3-diol, and also has the following names: trisamine, trometamol, and tromethane.

According to one embodiment of the present invention, the solvent of step a) is selected from the group consisting of isopropanol, propanol, methanol, butanol, tert-butanol, isobutanol, and mixtures of thereof.

The volume of solvent to be used in the process can be determined by the skilled person. Preferably a volume (in ml) between 1-50 times the amount of moles of (1R,3S)-3-(5-cyano-4-phenyl-1,3-thiazol-2-ylcarbamoyl)cyclopentane carboxylic acid is used, more preferably between 1-10 times.

The skilled person can determine, through rutinary procedures, when (1R,3S)-3-(5-cyano-4-phenyl-1,3-thiazol-2-ylcarbamoyl)cyclopentane carboxylic acid tromethamine salt has been formed, for example using thin layer chromatography, nuclear magnetic resonance or high performance liquid chromatography.

Once said salt is formed, step b) is carried out, ie, isolating the resulting tromethamine salt through usual processes in the field of the invention, for example, by filtration. In a particular embodiment, the mixture of step a) is cooled or allowed to cool between 15° to 30° C. before carrying out step b).

Preferably, step b) further comprises washing the resulting salt in order to remove impurities, and drying said salt. The washing is preferably carried out with the same solvent as used in step a). The drying is preferably carried out under vacuum and at room temperature.

Combinations and Pharmaceutical Compositions

The invention further provides a combination product comprising the salt of the invention and one or more therapeutic agents selected from: a) angiotensin converting enzyme inhibitors (ACE-inhibitors), b) angiotensin receptor antagonists, c) statins, d) beta blockers, e) calcium antagonists and f) diuretics.

Examples of ACE-inhibitors are, for example, captorpil, enalapril, and benazepril, among others.

Examples of antagonists of angiotensin receptor are, for example losartan, azilsartan, irbesartan, and eprosartan, among others.

Examples of statins are, for example, atorvastatin, fluvastatin, simvastatin, and lovastatin, among others.

Examples of beta-blockers are, for example, acebutol, atenolol, betaxolol, carvedilol, and propanolol, among others.

Examples of calcium antagonists are, for example, amlodipine, verapamil, vidipine, and isradipine, among others.

Examples of diuretics are, for example, chlorothiazide, chlorthalidone, furosemide, and spironolactone, among others.

Said combination product may be a pharmaceutical composition comprising the salt and the one or more therapeutic agents. Alternatively, in the combination product the salt and the one or more therapeutic agents are in different compositions.

Moreover, the invention also encompasses pharmaceutical compositions comprising the salt as defined above or a combination as defined above and a pharmaceutically acceptable excipient. In particular, tromethamine salt is in a therapeutically effective amount. The therapeutic agent, when present, is also preferably in a therapeutically effective amount.

An "effective amount" or "therapeutically effective amount" of a drug or pharmacologically active agent means a non-toxic but sufficient amount of the drug or agent to provide the desired effect. The amount that is "effective" will vary from subject to subject, depending on the age and general condition of the individual, the particular active agent or agents, and the like. Therefore, it is not always possible to specify an exact "effective quantity". However, an appropriate "effective" amount in any individual case can be determined by the skilled person using routine experimentation.

The salt of the present invention and the one or more therapeutic agents defined above may be administered simultaneously, sequentially or separately.

Simultaneous administration may, for example, take place in form of a composition comprising the salt of the present invention and one or more therapeutic agents defined above, or by simultaneous administration, ie administration at the same time, of the salt of the present invention and the one or more therapeutic agents defined above that are formulated independently, ie, when they are not part of the same composition.

Sequential administration preferably means administering the salt of the present invention, at a time point, and the one or more therapeutic agents defined above at a different time point, in a staggered manner.

Separate administration preferably means administration of the salt of the present invention and the one or more therapeutic agents defined above, independently of each other at different time points.

The term "pharmaceutically acceptable excipient" refers to a carrier, diluent, or adjuvant which is administered with the active ingredient. Such pharmaceutical excipients may be sterile liquids, such as water and oils, including those of petroleum, animal, vegetable, or synthetic origin, such as peanut oil, soybean oil, mineral oil, sesame oil, and the like. Water or aqueous salt solutions and aqueous solutions of dextrose and glycerol, particularly for injectable solutions, are preferably used as carriers. Suitable pharmaceutical carriers are described in "Remington Pharmaceutical Sciences" by E W Martin, 21' Edition, 2005.

Examples of pharmaceutically acceptable excipients for the oral dosage pharmaceutical compositions of the invention are conventional excipients known in the art such as binding agents, for example, syrup, gum arabic, gelatin, sorbitol, tragacanth or polyvinylpyrrolidone; fillers, for example, lactose, mannitol, xylitol, sorbitol, sucrose, corn starch, calcium phosphate, sorbitol, glycine, dextrose, maltodextrin, dextran, dextrin, modified starches; glidants and tablet lubricants, for example magnesium stearate, calcium stearate, stearic acid, zinc stearate, glyceryl monostearate, glyceryl palmitostearate, hydrogenated castor oil, colloidal silicon dioxide, silicon dioxide, anhydrous colloidal silicon, glycerine, hydrogenated vegetable oil, mineral oil, polyethylene glycol, sodium benzoate, sodium lauryl sulfate, sodium stearyl fumarate or talc; disintegrants, for example, starch, polyvinylpyrrolidone, starch sodium glycolate, crospovidone, microcrystalline cellulose, hydroxypropyl cellulose or sorbitan fatty acid esters; pharmaceutically acceptable wetting agents such as sodium lauryl sulfate; water solubilizing aids such as urea, betaine monohydrate, potassium sulfate, potassium acetate, mannitol; alkalinizing agents such as potassium carbonate, sodium carbonate, sodium bicarbonate, trisodium phosphate, tripotassium phosphate, trisodium citrate, tripotassium citrate; sweeteners such as saccharin sodium, sodium cyclamate and aspartame; flavoring agents such as menthol and peppermint oil.

Pharmaceutical compositions of the invention may be administered parenterally, orally or topically, preferably by oral route.

In a preferred embodiment, pharmaceutical compositions are in a dosage form suitable for parenteral administration, such as sterile solutions, suspensions or lyophilized products in the form of a suitable dosage unit. Suitable excipients such as fillers, buffering agents or surfactants may be used.

Pharmaceutical compositions may also be in oral form, either solid or liquid. Suitable dosage forms for oral administration may be tablets, capsules, syrups or powder solutions for solution or oral suspension, granules, sachets. Preferably the dosage form is selected from the group consisting of tablets and capsules.

The above formulations will be prepared using standard methods such as those described or contemplated in the Spanish and US pharmacopoeias and similar reference texts.

Medical Uses

Tromethamine salt object of the present invention exhibits/maintains a potent antagonist activity on the $A_1$ adenosine receptor.

Thus, the invention is also directed to the use of the salt as described above, a combination product of the salt of the invention together with one or more therapeutic agents as defined above or a pharmaceutical composition such as has been defined above, for use as a medicament.

This aspect may also be formulated as the salt of the invention as described above, a combination product of the salt of the invention together with one or more therapeutic agents as defined above or a pharmaceutical composition as defined above, to prepare a medicament.

Another aspect of the invention is addressed to the salt of the invention as described above, a combination product of the salt of the invention together with one or more therapeutic agents as defined above or a pharmaceutical composition such as has been defined above for use in the treatment and/or prevention of a disease known to ameliorate by $A_1$ adenosine receptor antagonism.

This aspect may also be formulated as the use of the salt of the invention as described above, a combination product of the salt of the invention together with one or more therapeutic agents as defined above or a pharmaceutical composition as defined previously, in the manufacture of a medicament for the treatment and/or prevention of a disease known to ameliorate by $A_1$ adenosine receptor antagonism.

This aspect may also be formulated as a method of treating and/or preventing a disease known to ameliorate by adenosine $A_1$ receptor antagonism, comprising administering to a subject in need of such treatment the salt of the invention as described above, a combination product of the salt of the invention together with one or more therapeutic agents as defined above or a pharmaceutical composition as defined above.

The disease or condition amenable to ameliorate by adenosine $A_1$ receptor antagonism is selected from hypertension, heart failure, ischemia, supraventricular arrhythmia, acute renal failure or any other disease caused by fluid retention, myocardial reperfusion injury, asthma, allergic reactions including but not limited to hypertension, heart failure, ischemia, supraventricular arrhythmia, acute renal failure, myocardial reperfusion injury, asthma, allergic reactions including rhinitis and urticaria, scleroderma and autoimmune diseases, such as multiple sclerosis. In a preferred embodiment, the disease or condition amenable to amelioration by $A_1$ adenosine receptor antagonism is selected from the group consisting of heart failure, acute renal failure, asthma, arterial hypertension, and intradialytic hypotension.

The terms "treat" and "treatment", as used herein, mean reversing, alleviating, inhibiting progression of the disease or condition to which said term or one or more symptoms of said disease or condition applies.

The terms "prevent" and "prevention," as used herein, mean the inhibition of the occurrence of the disease or condition to which this term applies or one or more symptoms of such disease or condition.

In use according to the invention, the salt of the invention, the combination product or the pharmaceutical composition may be administered 1, 2, 3, 4 or 5 times/day. In use, the salt of the invention, the combination product or the pharmaceutical composition may be administered until the symptoms of the disease or conditions to be treated are reversed, alleviated, or inhibited in their progress.

The following non-limiting examples are intended to illustrate the present invention and should not be considered as limitations of the scope of the same.

EXAMPLES

General

XRPD analyses were carried out under environmental conditions using a diffractometer PANalytical X'Pert with a reflection geometry θ-θ, radiation Cu Kα and detector PIXcel, at 45 kV and 40 mA. The samples were set up in a zero background silicon sample holder and were rotated at 0.25 rev/s during data acquisition. The measurements were registered at an angular range of 3-40° (2θ) with a step size of 0.013° at a scanning speed of 0.328°/s. Only peaks with an intensity equal or larger than 1% were reported.

$^1$H-NMR analysis were carried out in deuterated methanol (MeOD-$d_4$) or DMSO-$d_6$ as a solvent, in a Varian Mercury 400 equipped with a wide probe ATB 1H/19F/X of 5 mm. The spectrum was acquired dissolving 5-10 mg of the sample in 0.6 ml of deuterated solvent.

Stability studies under forced conditions were carried out by keeping the product under study for one week at 40° C. and 70% RH. Salts were analyzed by XRPD to check any change in the crystalline form.

Hygroscopicity studies of salts were carried out by preparation of Dynamic Vapour Sorption (DVS) profiles, with a TA instrument Q5000 apparatus. After an initial stabilization period (samples are pre-dried at 60° C. under vacuum), isotherms (at 25° C.) were obtained for each sample: a moisture sorption from 0 to 95% relative humidity (RH) and moisture desorption from 95% RH to dryness. Both isotherms were performed in 5% and 10% humidity steps.

The relative humidity (RH) was controlled by a mixture of wet and dry nitrogen stream. The RH was held constant until the equilibrium had been obtained (constant weight) or until the maximum time has been reached, before changing the RH to the next level.

Solubility screen assays were carried out as following: stock solutions ($10^{-2}$M) of the assayed compounds were diluted to decreased molarity from 500 μM to 0.256 nM, in 384 well transparent plate (Greiner 781101) with 5% DMSO: 95% PBS buffer. Samples were incubated at 37° C. and read after 2 and 4 hours in a NEPHELOstar Plus (BMGLABTECH). The results were adjusted to a segmented regression to obtain the maximum concentration in which compounds are soluble.

Example 1. Synthesis of (1R,3S)-3-(5-cyano-4-phenyl-1,3-thiazol-2-ylcarbamoyl)cyclopentane Carboxylic Acid The synthesis of compound (1R,3S)-3-(5-cyano-4-phenyl-1,3-thiazol-2-ylcarbamoyl)cyclopentane carboxylic acid is described in detail in patent application WO2009044250, which is incorporated herein by reference.

$^1$H-NMR (300 MHz, DMSO-$d_6$): δ=1.88 (m, 4H), 1.99 (m, 1H), 2.22 (m, 1H), 2.79 (m, 1H), 3.06 (m, 1H), 7.57 (m, 3H), 7.99 (m, 2H), 12.37 (s, 1H), 12.89 (s, 1H).

FIG. 1 illustrates DVS pattern of (1R-3S)-3-(5-cyano-4-phenyl-1,3-thiazol-2-ylcarbamoyl)cyclopentanecarboxylic acid (free acid form).

Example 2. Preparation of (1R,3S)-3-(5-cyano-4-phenyl-1,3-thiazol-2-ylcarbamoyl)cyclopentane Carboxylic Acid Tromethamine Salt A suspension of (1R,3S)-3-(5-cyano-4-phenyl-1,3-thiazol-2-ylcarbamoyl)cyclopentane carboxylic acid (100 mg, 0.293 mmol) and tromethamine (39.0 mg, 0.322 mmol) in isopropanol (IPA) (1.5 ml) was placed in a 10 ml flask equipped with magnetic stirring and a refrigerant. It was heated under reflux until a solution is obtained. Then, the solution was slowly cooled to room temperature and the suspension thus obtained was stirred at this temperature for two hours. The solid was filtered with No. 3 filter plate, washed with IPA (2×0.2 ml) and dried under vacuum at room temperature for hours affording 104.9 mg of (1R,3S)-3-(5-cyano-4-phenyl-1,3-thiazol-2-ylcarbamoyl)cyclopentane carboxylic acid tromethamine salt as a beige solid (75%).

$^1$H-NMR (400 MHz, MeOD-$d_4$): δ=8.11-8.09 (m, 2H); 7.51-7.45 (m, 3H); 3.64 (s, 6H); 3.1 (qt, J=8.0 Hz, 1H); 2.81 (qt, J=8.0 Hz, 1H); 2.29-2.21 (m, 1H); 2.17-2.10 (m, 1H); 2.03-1.97 (m, 4H).

The obtained crystalline form of (1R,3S)-3-(5-cyano-4-phenyl-1,3-thiazol-2-ylcarbamoyl)cyclopentane carboxylic acid tromethamine salt is characterized by a XRPD pattern, according is shown in the Table 1 above.

TABLE 1

| Pos. [°2Th] | Relative Intensity [%] |
|---|---|
| 8.7 | 100 |
| 12.3 | 3 |
| 13.0 | 4 |
| 13.4 | 1 |
| 16.3 | 2 |
| 16.8 | 1 |
| 17.3 | 2 |
| 18.0 | 8 |
| 18.4 | 9 |
| 19.5 | 2 |
| 20.9 | 5 |
| 21.7 | 6 |
| 23.8 | 1 |
| 24.6 | 5 |
| 26.1 | 8 |

Figure 2:
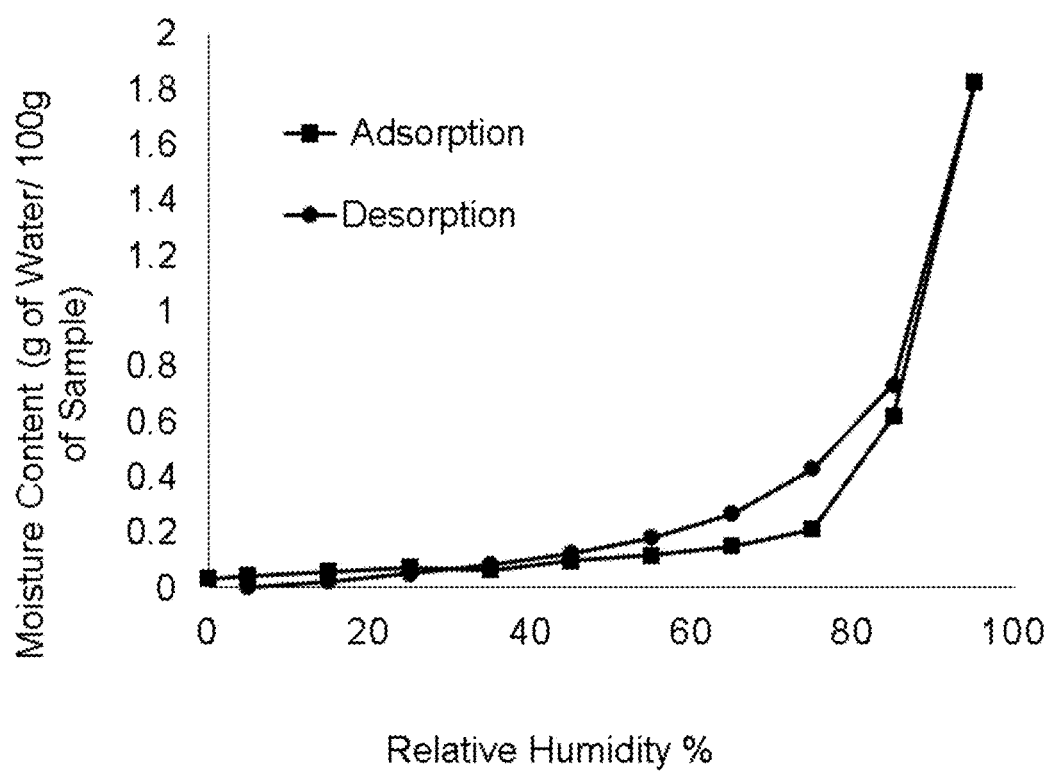
FIG. 2 illustrates DVS pattern of (1R,3S)-3-(5-cyano-4-phenyl-1,3-thiazol-2-ylcarbamoyl)cyclopentane carboxylic acid tromethamine salt, showing the change in weight (in %) of said salt as a function of relative humidity (RH).

FIG. 2 illustrates the DVS pattern of (1R,3S)-3-(5-cyano-4-phenyl-1,3-thiazol-2-ylcarbamoyl)cyclopentane carboxylic acid tromethamine salt. According to the results, said salt is less hygroscopic than the free acid form at usual drug storage conditions (<75% RH).

Figure 3:
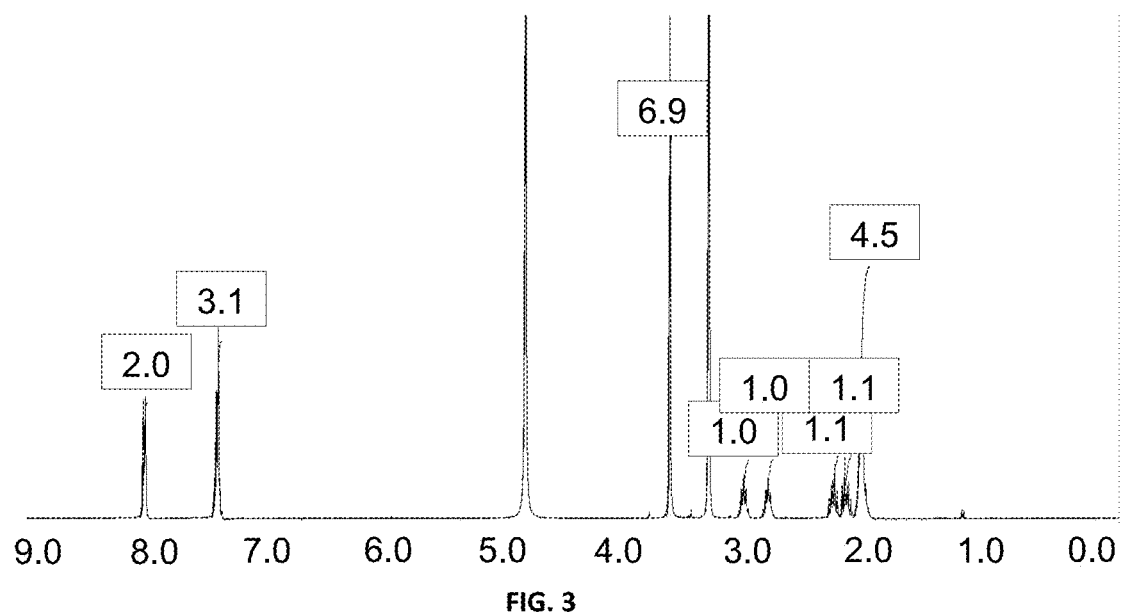
FIG. 3 shows $^1$H-NMR spectrum of (1R,3S)-3-(5-cyano-4-phenyl-1,3-thiazol-2-ylcarbamoyl)cyclopentane carboxylic acid tromethamine salt.

FIG. 3 shows the $^1$H-NMR spectrum of the obtained trometamine salt, confirming that (1R,3S)-3-(5-cyano-4-phenyl-1,3-thiazol-2-ylcarbamoyl)cyclopentane carboxylic acid and tromethamine are in a ratio of 1:1.

Figure 4:
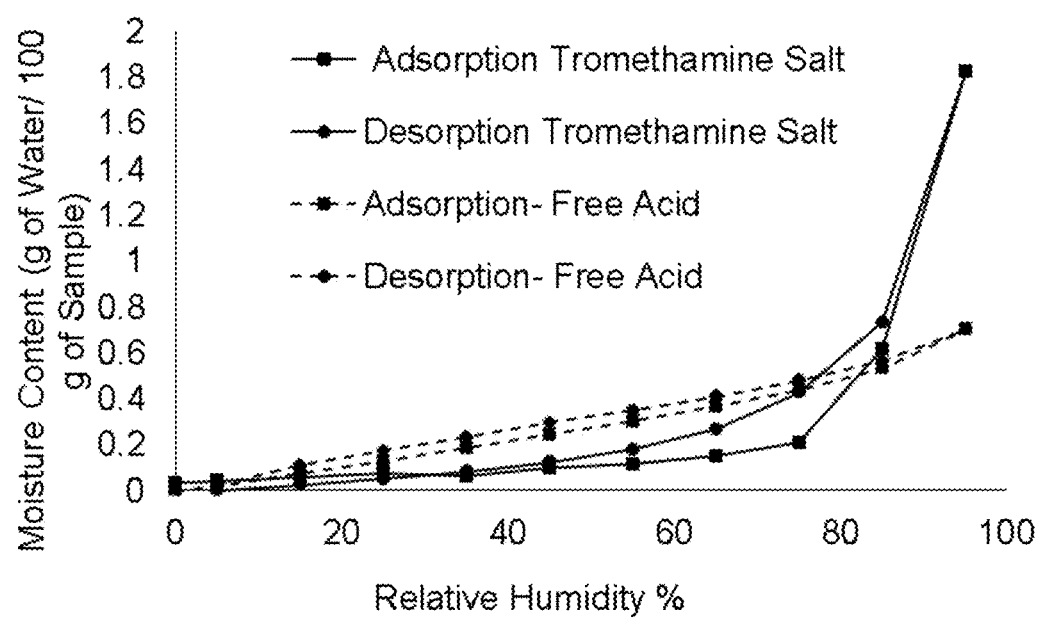
FIG. 4 illustrates a comparison between DVS patterns of (1R,3S)-3-(5-cyano-4-phenyl-1,3-thiazol-2-ylcarbamoyl) cyclopentane carboxylic acid and tromethamine salt thereof.

FIG. 4 shows a comparison between the DVS patterns of (1,3S)-3-(5-cyano-4-phenyl-1,3-thiazol-2-ylcarbamoyl)cyclopentane carboxylic acid and the tromethamine salt thereof.

Example 3. Preparation of (1R,3S)-3-(5-cyano-4-phenyl-1,3-thiazol-2-ylcarbamoyl)cyclopentane Carboxylic Acid Triethanolamine Salt (IUPAC Name: tris(hydroxyethyl)ammonium (1R,3S)-3-((5-cyano-4-phenylthiazol-2-yl)carbamoyl)cyclopentane-1-carboxylate)

To a solution of (1R,3S)-3-(5-cyano-4-phenyl-1,3-thiazol-2-ylcarbamoyl)cyclopentane carboxylic acid (100 mg, 0.293 mmol) in ethyl acetate (AcOEt) (1.5 ml) a solution of triethanolamine (43.7 mg, 0.293 mmol) in AcOEt (0.8 ml) was added at room temperature. In a short period of time, solid precipitated and the suspension thus obtained was stirred at room temperature for seven hours. The solid was filtered with No. 3 filter plate, washed with AcOEt (0.1 ml) and dried vacuum at room temperature for 15 hours to provide 121.7 mg of (1R,3S)-3-(5-cyano-4-phenyl-1,3-thiazol-2-ylcarbamoyl)cyclopentane carboxylic acid triethanolamine salt as a white solid (85% yield).

$^1$H NMR (400 MHz, DMSO-$d_6$) δ=7.99 (dd, 2H), 7.56 (dt, 3H), 4.46 (m, 3H), 3.42 (t, 6H), 3.08-3.00 (m, 1H), 2.82-2.73 (m, 1H), 2.58 (t, 6H), 2.24-2.15 (m, 1H), 2.03-1.95 (m, 1H), 1.93-1.79 (m, 4H).

The obtained crystalline form of (1R,3S)-3-(5-cyano-4-phenyl-1,3-thiazol-2-ylcarbamoyl)cyclopentane carboxylic acid triethanolamine salt is characterized by X-ray powder diffraction (XRPD) pattern with the following peaks: 5.29, 6.88, 8.89, 9.08, 10.27, 10.60, 11.89, 12.78, 13.07, 13.80, 14.26, 15.05, 16.63, 17.03, 18.10, 18.47, 19.44, 19.98, 20.61, 21.75, 22.63, 24.09, 24.51, 25.10, 25.42, 25.80, 26.41, 26.90, 27.63, 30.41, 34.54±0.20 degrees 2θ.

Figure 5:
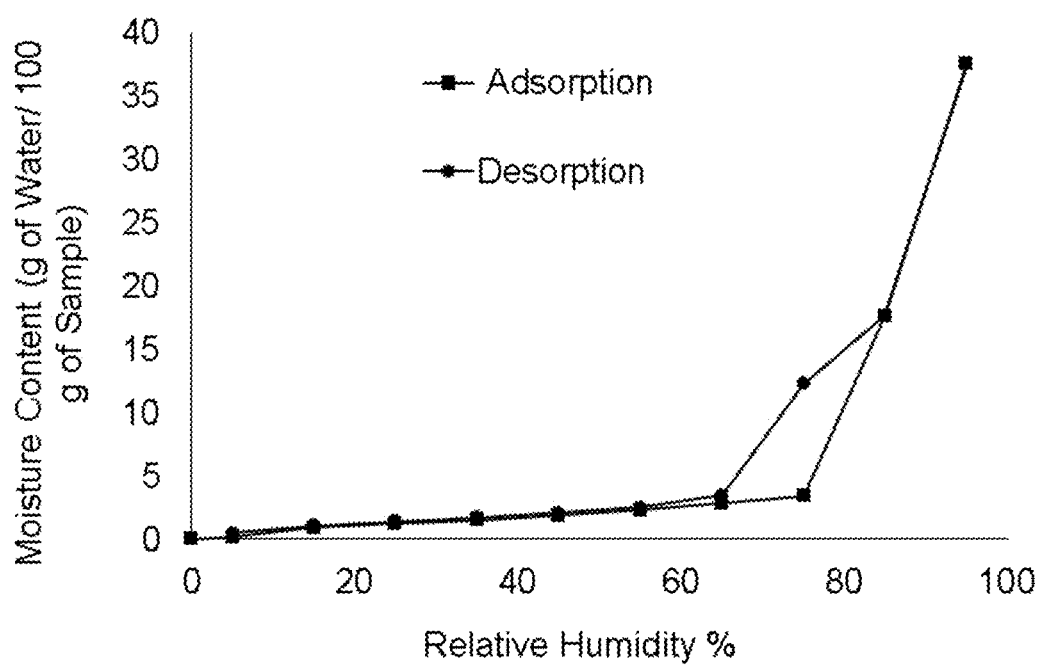
FIG. 5 illustrates DVS pattern of (1R-3S)-3-(5-cyano-4-phenyl-1,3-thiazol-2-ylcarbamoyl)cyclopentane carboxylic acid triethanolamine salt, showing the change in weight (in %) of said salt as a function of relative humidity (RH).

FIG. 5 illustrates DVS pattern of (1R,3S)-3-(5-cyano-4-phenyl-1,3-thiazol-2-ylcarbamoyl)cyclopentane carboxylic acid triethanolamine salt. The results indicate that said salt is moderately hygroscopic at up to 75% RH. From 0 to 75%

RH the weight increases a 3.44%. Above 75% RH, the water adsorption shoots up sharply to reach 17.58% at 85% RH and 37.48% at 95% RH.

Figure 6:
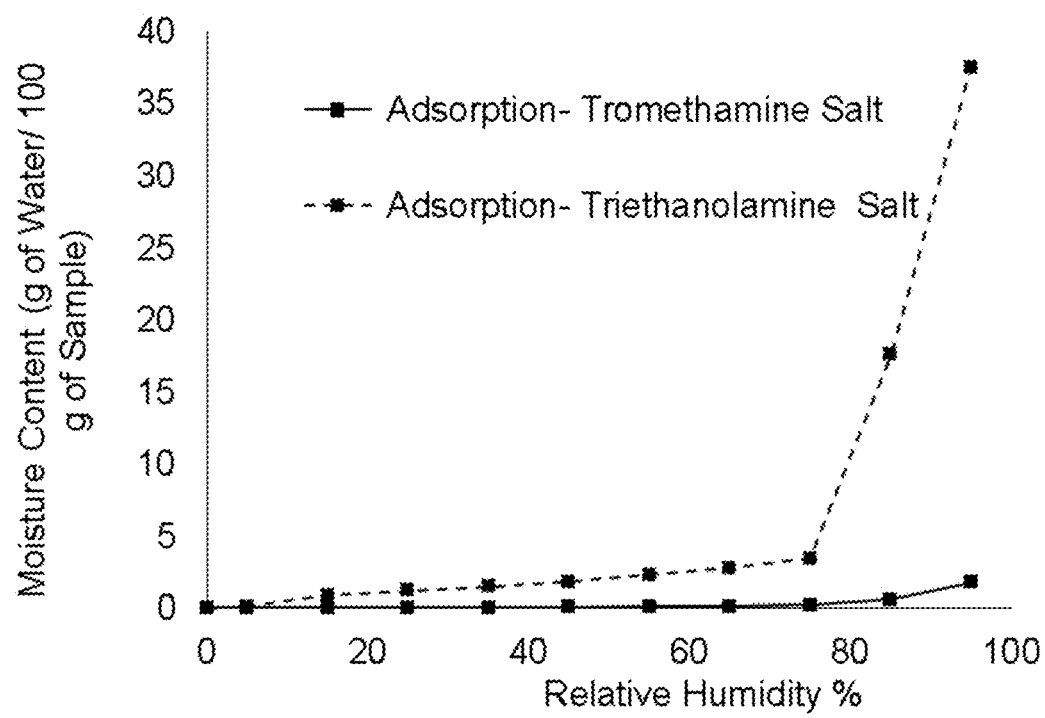
FIG. 6 illustrates a comparison between DVS patterns of (1R,3S)-3-(5-cyano-4-phenyl-1,3-thiazol-2-ylcarbamoyl) cyclopentane carboxylic acid tromethamine salt and triethanolamine salt.

According to the results, this salt is more hygroscopic than the free acid form and than the tromethamine salt, at usual drug storage conditions (<75% RH). FIG. 6 shows a comparison between DVS patterns of (1R,3S)-3-(5-cyano-4-phenyl-1,3-thiazol-2-ylcarbamoyl)cyclopentane carboxylic acid tromethamine salt and the triethanolamine salt.

Example 4. Preparation of (1R,3S)-3-(5-cyano-4-phenyl-1,3-thiazol-2-ylcarbamoyl)cyclopentane Carboxylic Acid Diethylamine Salt (IUPAC Name: Diethylammonium (1R,3S)-3-((5-cyano-4-phenylthiazol-2-yl)carbamoyl)cyclopentane-1-carboxylate)

To a solution of (1R,3S)-3-(5-cyano-4-phenyl-1,3-thiazol-2-ylcarbamoyl)cyclopentanecarboxylic acid (100 mg, 0.293 mmol) in ethanol (EtOH) (1.35 ml) diethylamine 0.5 M solution in EtOH (0.65 ml, 0.293 mmol) was added. The resulting solution was allowed to slowly evaporate at room temperature for two days to obtain a fine solid. The solid was dried under vacuum at room temperature for 15 hours giving 105 mg of (1R,3S)-3-(5-cyano-4-phenyl-1,3-thiazol-2-ylcarbamoyl)cyclopentane carboxylic acid diethylamine salt as a beige solid.

$^1$H NMR (400 MHz, DMSO-$d_6$) δ=7.99 (d, 2H), 7.56-7.44 (m, 3H), 2.95-2.88 (m, 1H), 2.84 (q, 4H), 2.75-2.68 (m, 1H), 2.13-1.96 (m, 2H), 1.84 (m, 4H), 1.12 (t, 6H).

The obtained crystalline form of (1R,3S)-3-(5-cyano-4-phenyl-1,3-thiazol-2-ylcarbamoyl)cyclopentane carboxylic acid diethylamine salt is characterized by X-ray powder diffraction (XRPD) pattern with the peaks at: 5.51, 7.03, 9.23, 11.07, 12.11, 12.38, 13.14, 15.22, 15.64, 16.45, 17.26, 18.17, 19.22, 19.56, 19.95, 21.41, 22.71, 24.92, 25.35, 26.68, 28.34±0.20 degrees 2θ.

Example 5. Preparation of Sodium Salt of (1R,3S)-3-(5-cyano-4-phenyl-1,3-thiazol-2-ylcarbamoyl)cyclopentane Carboxylic Acid (IUPAC name: Sodium (1R,3S)-3-((5-cyano-4-phenylthiazol-2-yl)carbamoyl)cyclopentane-1-carboxylate)

A solution of (1R,3S)-3-(5-cyano-4-phenyl-1,3-thiazol-2-ylcarbamoyl)cyclopentane carboxylic acid (200 mg, 0.586 mmol) and NaOH (25.7 mg, 0.642 mmol) in acetonitrile (ACN) (2.0 ml) was placed in a 10 ml flask equipped with magnetic stirring and was stirred at room temperature for one hour. The solid was filtered with No. 3 filter plate, washed with ACN (2×0.4 ml) and vacuum dried at room temperature for 15 hours to provide 178.1 mg of (1R,3S)-3-(5-cyano-4-phenyl-1,3-thiazol-2-ylcarbamoyl)cyclopentane carboxylic acid sodium salt as a white solid (83%).

$^1$H NMR (400 MHz, DMSO-$d_6$) δ=7.99 (d, 2H), 7.49 (m, 3H), 2.93-2.84 (m, 1H), 2.72 (m, 1H), 2.04 (m, 2H), 1.84 (d, 4H).

The obtained crystalline form of the sodium salt of (1R,3S)-3-(5-cyano-4-phenyl-1,3-thiazol-2-ylcarbamoyl)cyclopentane carboxylic acid is characterized by X-ray powder diffraction (XRPD) pattern with peaks at: 3.65, 7.24, 9.76, 11.08, 12.24, 12.84, 14.32, 16.11, 17.00, 19.29, 20.00, 21.33, 22.31, 23.24, 25.00, 25.56, 26.66, 28.18, 31.04, 32.69±0.20 degrees 2θ.

Example 6. Preparation of magnesium salt of (1R, 3S)-3-(5-cyano-4-phenyl-1,3-thiazol-2-ylcarbamoyl)cyclopentane Carboxylic Acid (IUPAC Name: Magnesium (1R,3S)-3-((5-cyano-4-phenylthiazol-2-yl)carbamoyl)cyclopentane-1-carboxylate)

To a solution of (1R,3S)-3-(5-cyano-4-phenyl-1,3-thiazol-2-ylcarbamoyl)cyclopentane carboxylic acid (100 mg, 0.293 mmol) and NaOH 2M (0.160 mL, 0.320) in $H_2O$ (1 mL $MgCl_2.6H_2O$ (30.0 mg, 0.147 mmol) was added. To the precipitate thus obtained $H_2O$ (1 mL) was added to prepare a homogeneous solution which was stirred at room temperature for 90 minutes. The solid was filtered with No. 3 filter plate, washed with $H_2O$ (2×0.2 mL) and vacuum dried at room temperature for 15 hours, to provide 73.9 mg of magnesium salt of (1R,3S)-3-(5-cyano-4-phenyl-1,3-thiazol-2-ylcarbamoyl)cyclopentane carboxylic acid as a solid color beige (71%).

$^1$H NMR (400 MHz, DMSO-$d_6$) δ=7.99 (d, 4H), 7.51 (m, 6H), 2.91 (m, 2H), 2.67 (m, 2H), 2.18-1.96 (m, 4H), 1.84 (s, 8H).

The obtained crystalline form of the magnesium salt of (1R,3S)-3-(5-cyano-4-phenyl-1,3-thiazol-2-ylcarbamoyl)cyclopentane carboxylic acid is characterized by X-ray powder diffraction (XRPD) pattern with the peaks at: 4.08, 7.23, 8.68, 10.76, 18.17, 25.14±0.20 degrees 2θ.

Figure 7:
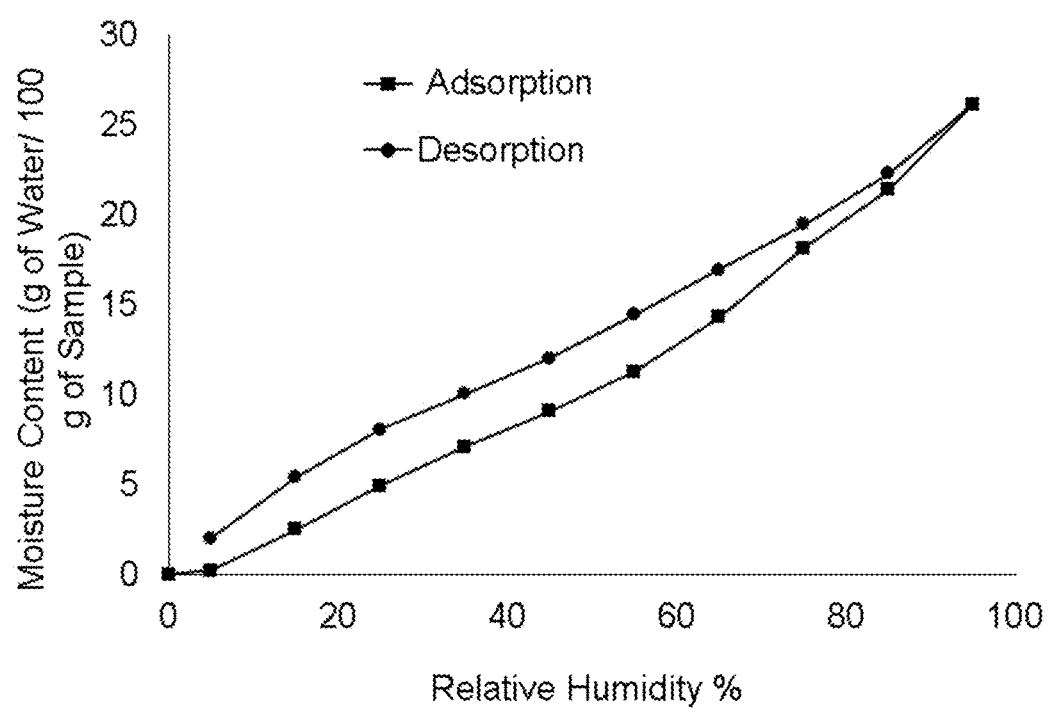
FIG. 7 illustrates DVS pattern of (1R,3S)-3-(5-cyano-4-phenyl-1,3-thiazol-2-ylcarbamoyl)cyclopentane carboxylic acid magnesium salt, showing the change in weight (in %) of said salt as a function of relative humidity (RH).

FIG. 7 illustrates DVS pattern of the magnesium salt of (1R,3S)-3-(5-cyano-4-phenyl-1,3-thiazol-2-ylcarbamoyl)cyclopentane carboxylic acid, showing that said salt is very hygroscopic. The moisture content is proportional to the % RH and rises to 18.11% at 75% RH.

The table below (Table 2) shows the moisture content of three different salts and the parent carboxylic acid measured in the hygroscopicity study.

TABLE 2

| Compounds | 25% RH | 55% RH | 75% RH |
|---|---|---|---|
| (1R-3S)-3-(5-cyano-4-phenyl-1,3-thiazol-2-ylcarbamoyl)cyclopentane carboxylic acid | 0.1283 | 0.3008 | 0.4369 |
| (1R-3S)-3-(5-cyano-4-phenyl-1,3-thiazol-2-ylcarbamoyl)cyclopentane carboxylic acid tromethamine salt | 0.0722 | 0.1165 | 0.2096 |
| (1R-3S)-3-(5-cyano-4-phenyl-1,3-thiazol-2-ylcarbamoyl)cyclopentane carboxylic acid triethanolamine salt | 1.238 | 2.308 | 3.443 |
| magnesium salt of (1R,3S)-3-(5-cyano-4-phenyl-1,3-thiazol-2-ylcarbamoyl)cyclopentane carboxylic acid | 4.929 | 11.27 | 18.11 |

As it can be seen from the above table, tromethamine salt is less hygroscopic than free acid, specially up to 75% RH. A structurally similar salt, as triethanolamine salt, is considerably more hygroscopic than tromethamine salt.

Example 7. Solubility Screen Assay

The solubility of Examples 1-5 at 37° C. are shown in Table 3 below.

TABLE 3

| Compounds | Solubility (μM) |
|---|---|
| (1R-3S)-3-(5-cyano-4-phenyl-1,3-thiazol-2-ylcarbamoyl)cyclopentane carboxylic acid | 0.08 |

TABLE 3-continued

| Compounds | Solubility (μM) |
|---|---|
| (1R-3S)-3-(5-cyano-4-phenyl-1,3-thiazol-2-ylcarbamoyl)cyclopentane carboxylic acid tromethamine salt | 71.0 |
| (1R-3S)-3-(5-cyano-4-phenyl-1,3-thiazol-2-ylcarbamoyl)cyclopentane carboxylic acid triethanolamine salt | 1.3 |
| (1R-3S)-3-(5-cyano-4-phenyl-1,3-thiazol-2-ylcarbamoyl)cyclopentane carboxylic acid diethylamine salt | 8.1 |
| sodium salt of (1R-3S)-3-(5-cyano-4-phenyl-1,3-thiazol-2-ylcarbamoyl)cyclopentane carboxylic acid | 36.3 |

As it can be seen from the above table, tromethamine salt presents higher solubility compared to others salts, even with structurally similar salts and free acid.

Example 8. Oral Bioavailability Assays

The objective of this study was to investigate the plasma pharmacokinetics of differentes salts obtained from (1R,3S)-3-(5-cyano-4-phenyl-1,3-thiazol-2-ylcarbamoyl)cyclopentanecarboxylic acid, following a single intravenous (IV) and oral (PO) administration in male SD rats.

Animals were divided into two groups: Group 1 (IV: 1 mg/kg) and Group 2 (PO: 5 mg/kg). Animals in Group 1 and 2 were administered a solution of the different salts of (1R,3S)-3-(5-cyano-4-phenyl-1,3-thiazol-2-ylcarbamoyl)cyclopentane carboxylic acid in normal saline. The blood samples were collected from set of three rats at each time point in labeled micro centrifuge tube containing $K_2EDTA$ solution as anticoagulant at Pre-dose, 0.083, 0.25, 0.5, 1, 2, 4, 8 and 24 hr (IV) and Pre-dose, 0.25, 0.5, 1, 2, 4, 6, 8 and 24 hr (PO). Plasma samples were separated by centrifugation of whole blood and stored below −70±10° C. until bioanalysis. All samples were processed for analysis by protein precipitation using acetonitrile and analyzed with fit-for-purpose LC-MS/MS method (LLOQ=1.00 ng/ml). Pharmacokinetic parameters were calculated using the non-compartmental analysis tool of Phoenix WinNonlin® (Version 6.3).

Main pharmacokinetic parameters obtained from Examples 1-5 are shown in Table 4 below.

TABLE 4

| Compound | Route | Dose (mg/Kg) | Cmax (ng/ml) | AUC last (ng/ml * hr) | Clearance (ml/min/kg) | F % |
|---|---|---|---|---|---|---|
| (1R,3S)-3-(5-cyano-4-phenyl-1,3-thiazol-2-ylcarbamoyl)cyclopentane carboxylic acid | iv | 1 | — | 2204.38 | 6.3 | — |
|  | po | 5 | 2012 | 5200.71 | — | 47 |
| (1R,3S)-3-(5-cyano-4-phenyl-1,3-thiazol-2-ylcarbamoyl)cyclopentane carboxylic acid tromethamine salt | iv | 1 | — | 2373.87 | 7.11 | — |
|  | po | 5 | 10952.45 | 14100.62 | — | 100 |
| (1R,3S)-3-(5-cyano-4-phenyl-1,3-thiazol-2-ylcarbamoyl)cyclopentane carboxylic acid triethanolamine salt | iv | 1 | — | 3521.23 | 4.85 | — |
|  | po | 5 | 4532.19 | 9304.80 | — | 53 |
| (1R,3S)-3-(5-cyano-4-phenyl-1,3-thiazol-2-ylcarbamoyl)cyclopentane carboxylic acid diethylamine salt | iv | 1 | — | 3383.00 | 5.02 | — |
|  | po | 5 | 5906.53 | 11580.30 | — | 68 |
| sodium salt of (1R,3S)-3-(5-cyano-4-phenyl-1,3-thiazol-2-ylcarbamoyl)cyclopentane carboxylic acid | iv | 1 | — | 5085.10 | 3.31 | — |
|  | po | 5 | 13153.47 | 21597.99 | — | 85 |

Cmax refers to the maximum plasma drug concentration obtained after oral administration of a drug between the time of dosing and the final observed time point.

AUC last refers to the area under the curve from the time of dosing to the time of last observation that is greater than the limit of quantitation.

Clearance refers to the measurement of the ability of the body to remove drug from the plasma, and is calculated from the intravenous dosing.

F % refers to the bioavailability. The systemic availability of a compound after oral administration is calculated using the following equation:

$$F(\%) = (AUClast\ PO \times Dose\ IV / AUClast\ IV \times Dose\ PO) \times 100$$

As it can be seen from the above table, tromethamine salt presents higher bioavailability compared to others salts, even with structurally similar salts and free acid.

The invention claimed is:

1. A tromethamine salt of (1R,3S)-3-(5-cyano-4-phenyl-1,3-thiazol-2-ylcarbamoyl)cyclopentane carboxylic acid.

2. The salt according to claim 1, wherein tromethamine and (1R,3S)-3-(5-cyano-4-phenyl-1,3-thiazol-2-ylcarbamoyl)cyclopentane carboxylic acid are in a 1:1 molar ratio.

3. The salt according to claim 1, characterized by being in a crystalline form having an X-ray powder diffraction pattern comprising 2θ° peaks at 8.7, 18.0, 18.4, 21.7 and 26.1±0.20 2θ°.

4. The salt according to claim 3, further comprising 2θ° peaks in the X-ray powder diffraction pattern at 12.3, 13.0, 13.4, 16.3, 16.8, 17.3, 19.5, 20.9, 23.8 and 24.6±0.20 2θ°.

5. A process for the preparation of the tromethamine salt of claim 1, comprising:
   a) mixing (1R,3S)-3-(5-cyano-4-phenyl-1,3-thiazol-2-yl-carbamoyl)cyclopentane carboxylic acid and tromethamine in presence of a solvent, and
   b) isolating the (1R,3S)-3-(5-cyano-4-phenyl-1,3-thiazol-2-ylcarbamoyl) cyclopentane carboxylic acid tromethamine salt obtained in step a).

6. The process according to claim 5, wherein the mixture of step a) is heated at the reflux temperature of the solvent.

7. The process according to claim 5, wherein the solvent is selected from the group consisting of alkanols, aliphatic hydrocarbons, aromatic hydrocarbons, ethers, ketones, esters, dichloromethane, chloroform, dimethylsulfoxide, acetonitrile, water, and mixtures thereof.

8. The process according to claim 7, wherein the solvent is selected from the group consisting of isopropanol, propanol, ethanol, methanol, butanol, tert-butanol, isobutanol, and mixtures thereof.

9. A combination product comprising the salt of claim 1 and one or more therapeutic agents selected from the group consisting of angiotensin converting enzyme inhibitors, angiotensin receptor antagonists, statins, beta-blockers, calcium antagonists, and diuretics.

10. A pharmaceutical composition comprising the salt of claim 1 and a pharmaceutically acceptable excipient.

11. A method of treating a disease known to be ameliorated by adenosine A1 receptor antagonism, comprising administering to a subject in need of such treatment the salt of claim 1.

12. The method according to claim 11, wherein the disease known to be ameliorated by A1 adenosine receptor antagonism is selected from the group consisting of hypertension, heart failure, ischemia, supraventricular arrhythmia, acute renal failure, myocardial reperfusion injury, asthma, allergic reactions scleroderma, and autoimmune diseases.

13. The method according to claim 12, wherein the disease known to be ameliorated by A1 adenosine receptor antagonism is selected from the group consisting of heart failure, acute renal failure, asthma, arterial hypertension, and intradialytic hypotension.

14. A pharmaceutical composition comprising the combination product of claim 9 and a pharmaceutically acceptable excipient.

15. A method of treating a disease known to be ameliorated by adenosine A1 receptor antagonism, comprising administering to a subject in need of such treatment the combination product of claim 9.

16. A method of treating a disease known to be ameliorated by adenosine A1 receptor antagonism, comprising administering to a subject in need of such treatment the pharmaceutical composition of claim 10.

17. The method of claim 12, wherein the allergic reactions are selected from rhinitis and urticaria.

* * * * *